(12) United States Patent
Berner

(10) Patent No.: US 9,603,700 B2
(45) Date of Patent: Mar. 28, 2017

(54) INTRACORNEAL LENS

(71) Applicant: Neoptics AG, Hünenberg (CH)

(72) Inventor: Werner Berner, Erlinsbach (CH)

(73) Assignee: PRESBIA IRELAND LIMITED, Dublin (IE)

(*) Notice: Subject to any disclaimer, the term of this patent is extended or adjusted under 35 U.S.C. 154(b) by 0 days.

(21) Appl. No.: 14/397,518

(22) PCT Filed: May 7, 2013

(86) PCT No.: PCT/EP2013/059473
§ 371 (c)(1),
(2) Date: Oct. 28, 2014

(87) PCT Pub. No.: WO2013/171097
PCT Pub. Date: Nov. 12, 2013

(65) Prior Publication Data
US 2015/0134058 A1    May 14, 2015

(30) Foreign Application Priority Data
May 14, 2012  (EP) .................... 12167842

(51) Int. Cl.
*A61F 2/14* (2006.01)
*A61F 2/00* (2006.01)
*A61F 2/16* (2006.01)
(52) U.S. Cl.
CPC ............ *A61F 2/145* (2013.01); *A61F 2/0095* (2013.01); *A61F 2/148* (2013.01); *A61F 2/1453* (2015.04); *A61F 2/1678* (2013.01); *A61F 2220/0025* (2013.01); *A61F 2250/0053* (2013.01); *A61F 2250/0089* (2013.01)

(58) Field of Classification Search
CPC ......................................... A61F 2/145–2/1453
USPC ................................. 623/5.11–5.16
See application file for complete search history.

(56) References Cited

U.S. PATENT DOCUMENTS 5,123,921 A    6/1992  Werblin
5,196,026 A    3/1993  Barrett et al.
(Continued)

FOREIGN PATENT DOCUMENTS

EP    1001720    5/2000
EP    1778141    5/2007
(Continued)

*Primary Examiner* — Paul Prebilic
(74) *Attorney, Agent, or Firm* — Davis & Bujold; Lawrence S. Cohen

(57) ABSTRACT

The present invention relates to an intracorneal lens (1), comprising a circular main body having a convex front surface and a convex rear surface, characterized in that the convex front surface has a single uniform radius of curvature (Rcv) and the concave rear surface has a radius of curvature (Rcci). The radius of curvature (Rcci) of the concave rear surface is greater than the average radius of the cornea by 0.1 mm to 2 mm, preferably 0.2 to 1.5 mm, in particular preferably 0.5 to 1 mm. The present invention further relates to a kit, comprising a storage unit (15) and a pre-load unit (P) inside the storage unit (15). The storage unit (15) is made of a watertight material and can be closed watertight by means of a plug (16). The pre-load unit (P) is fitted with the intracorneal lens according to the invention.

8 Claims, 6 Drawing Sheets

(56) References Cited

U.S. PATENT DOCUMENTS

Figure 1:
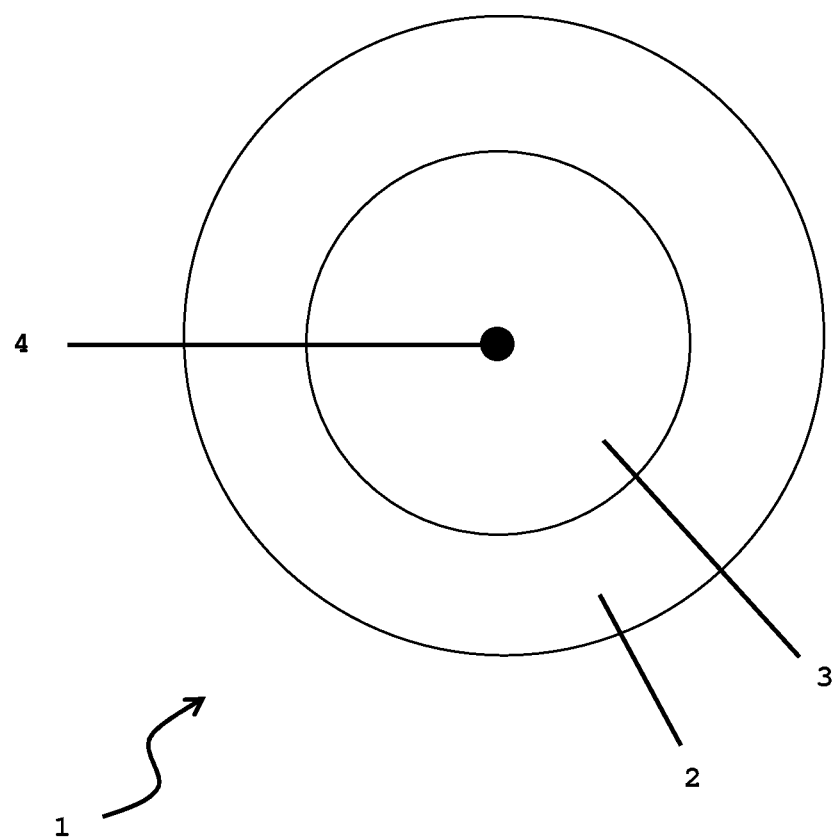

| | | | |
|---|---|---|---|
| 5,521,656 A * | 5/1996 | Portney | A61F 2/1618 351/159.74 |
| 5,628,794 A | 5/1997 | Lindstrom | |
| 6,099,121 A * | 8/2000 | Chapman | G02C 7/04 351/159.02 |
| 2002/0044255 A1 * | 4/2002 | Ye | G02C 7/042 351/159.1 |
| 2003/0014042 A1 | 1/2003 | Juhasz et al. | |
| 2004/0088049 A1 * | 5/2004 | LaCombe | A61F 2/142 623/5.14 |
| 2005/0246015 A1 | 11/2005 | Miller | |
| 2006/0116762 A1 * | 6/2006 | Hong | A61F 2/147 623/5.16 |
| 2007/0203577 A1 * | 8/2007 | Dishler | A61F 2/147 623/5.11 |
| 2009/0198325 A1 * | 8/2009 | Holliday | A61F 2/147 623/5.11 |
| 2011/0218623 A1 * | 9/2011 | Dishler | A61F 2/147 623/5.11 |
| 2012/0245683 A1 * | 9/2012 | Christie | A61F 2/145 623/5.11 |
| 2012/0323319 A1 * | 12/2012 | Cohen | A61F 2/145 623/5.11 |

FOREIGN PATENT DOCUMENTS

| | | | | |
|---|---|---|---|---|
| WO | 2008/072092 | 6/2008 | | |
| WO | 2009/075685 | 6/2009 | | |
| WO | WO 2011/055066 A1 * | 5/2011 | | A61F 2/14 |
| WO | 2011/069907 | 6/2011 | | |

* cited by examiner

INTRACORNEAL LENS

The present invention relates to an intracorneal lens for the correction of impaired vision, for example presbyopia.

Intracorneal lenses are used for the correction of impaired vision. In contrast to contact lenses, which are placed on the surface of the eye, and to intraocular lenses, which are implanted in a chamber of the eye, intracorneal lenses are inserted into a pocket created in the cornea. Intracorneal lenses differ significantly from contact lenses or intraocular lenses, for example in terms of their size, in the absence of holding elements (haptic elements) required for intraocular lenses, and in their optical properties.

Intracorneal lenses are known from the prior art. By way of example, reference is made to WO 2009/075685, U.S. Pat. No. 5,628,794, U.S. Pat. No. 5,123,921 or EP 1 001 720 B1.

WO 2009/075685 describes an intracorneal lens having a central hole. The central hole is concentric to the optical axis of the lens and is of such a size and shape that, while the optical properties of the lens are not impaired, the hole can nevertheless be used at the same time for more precise positioning of the lens in the corneal pocket.

However, it has been shown that these lenses do not yet provide optimal correction of sight in humans.

There was therefore a need for an intracorneal lens with which it is possible to better restore the visual acuity of persons with impaired vision, for example presbyopia.

According to the invention, the above object was achieved by an intracorneal lens comprising a circular main body with a convex front surface and a concave rear surface, characterized in that the convex front surface has a single uniform radius of curvature Rcv and the concave rear surface has a radius of curvature Rcci, wherein the radius of curvature Rcci of the concave rear surface is greater than the average radius of the cornea by 0.1 mm to 2 mm, preferably by 0.2 to 1.5 mm, particularly preferably by 0.5 to 1 mm.

It has been found, surprisingly, that a pronounced improvement in the correction of vision by intracorneal lenses can be achieved if the radius of curvature Rcci of the concave rear surface of the lens slightly exceeds the average radius of the cornea. In this way, on account of its low inherent stiffness, the lens according to the invention easily conforms to the cornea and exerts less force on the cornea. At the same time, however, it was found that the radius of curvature Rcci of the concave rear surface of the lens ought only to exceed the average radius of the cornea by a defined low value, since otherwise there may be formation of folds in the cornea at the outer edges of the lens, with associated negative optical effects.

According to the present invention, the radius of curvature Rcci of the concave rear surface is greater than the average radius of the cornea by 0.1 mm to 2 mm, preferably by 0.2 to 1.5 mm, particularly preferably by 0.5 to 1 mm.

It was also found that the provision of lens zones with different radii of curvature is possible by arranging the different radii of curvature on the concave rear surface of the lens, while the convex front surface of the lens has a single uniform radius of curvature Rcv. Because of the significant difference in the refractive indices of the cornea and of air, a change in the curvature of the cornea brought about by different radii of curvature of the implanted intracorneal lens has a considerable influence on the optical properties of the corrected eye on the outside of the cornea (interface to the environment), whereas an analogous change in the curvature of the cornea at the interface to the interior of the eye has an influence that is less by about a factor of 5 (less difference in the refractive indices of the cornea and of the vitreous humor).

As a result of the above measures, much better and more precise correction of visual acuity can be achieved with the intracorneal lens according to the invention than is possible with conventional intracorneal lenses. With the intracorneal lens according to the invention, it is possible to correct impaired vision such as myopia (short-sightedness), hyperopia (long-sightedness), presbyopia (age-related diminution of the accommodation of the eye) or a combination of these sight problems. With the surfaces of the lens suitably optimized in a manner known to a person skilled in the art, it is also possible to treat astigmatism with the aid of the intracorneal lens according to the invention.

The advantage of correcting these sight problems using the intracorneal lens according to the invention is that the correction can be made reversible by removing the lens from the cornea. Compared to conventional means of correction such as eyeglasses or contact lenses, the intracorneal lenses according to the invention have the advantages of not being visible, of avoiding wearing problems, of avoiding the misting up of eyeglasses under certain environmental conditions, and of avoiding the irritation of the cornea which can occur when wearing contact lenses.

The intracorneal lens according to the invention has a circular and dome-shaped main body with a diameter in the range of 2.4 to 4 mm, preferably of 2.7 to 3.5 mm, particularly preferably of 3 mm.

The intracorneal lens according to the invention is preferably made of a biocompatible material which permits the passage of nutrient liquids and other eye constituents and also permits sufficient gas diffusion (especially of oxygen). Biocompatible and permeable materials of this kind are known to a person skilled in the art. Examples that may be mentioned are silicones, hydrogels such as Perfilcon A®, urethanes or acrylates such as polymethacrylates. In the preferred embodiment of an intracorneal lens according to the invention with a central opening, the passage of liquids and gases through the lens is additionally facilitated by the central opening.

An essential aspect of the intracorneal lens according to the invention concerns the radii of curvature of the convex front surface and of the concave rear surface. According to the present invention, all the radii indicated relate to the lens in the hydrated state, i.e. the state of the lens when it is implanted in the corneal pocket.

As has been mentioned above, the convex front surface of the lens has a single uniform radius of curvature. In the case of a preferred bifocal lens according to the invention for the correction of presbyopia, the radius of curvature of the convex front surface preferably lies in a range of 7.5 to 8 mm. However, depending on the application, another radius of curvature may be chosen, such that the optical correction afforded by the actual lens according to the invention can be supported by a change in the curvature of the outer surface of the cornea.

As has been mentioned above, the concave rear surface of the lens according to the invention has a radius of curvature Rcci, which slightly exceeds the average radius of the cornea. The average radius of the cornea varies slightly from one individual to another and generally lies in a range of 7.4 mm to 8.1 mm, being typically about 7.8 mm. The radius of curvature Rcci of the concave rear surface of the lens according to the invention exceeds the average radius of the cornea by 0.1 mm to 2 mm, preferably by 0.2 to 1.5 mm, particularly preferably by 0.5 to 1 mm.

For correction of some sight problems, it is necessary for the lens according to the invention to be equipped with several different zones having different optical power. According to the invention, these zones are preferably provided by varying the radius of curvature of the rear surface of the lens, such that the zones have different thickness and different surface radii on the reverse. As has already been mentioned above, the different radii of curvature in the lens according to the invention are provided on the concave rear surface. By changing the radius of curvature of the lens surface, a change is brought about in the curvature of the cornea, and this change influences the visual acuity of the person being treated. A change in the curvature of the outer surface of the cornea has a much greater influence on visual acuity, since the refractive index of the cornea differs considerably from the refractive index of air. By contrast, the difference in the refractive indices of the cornea and of the liquid in the interior of the eye is much less. Consequently, a change in the curvature of the inner surface of the cornea has an effect on visual acuity that is less by about a factor of 5 than a corresponding change in the curvature of the outer surface of the cornea. By maintaining a uniform radius of curvature of the front convex surface of the lens and modifying the radius of curvature of the rear concave surface of the lens, it is possible to achieve a more precise adjustment of the desired visual acuity.

If the lens according to the invention is made available with several different zones having different radii of curvature, it is important that the lens conforms to the cornea, as has been described above. The different radii of curvature must therefore be chosen such that this important aspect of the invention is achieved. It is preferably achieved by virtue of the fact that all of the different zones of radii of curvature are chosen such that each of these radii of curvature is greater than the average radius of the cornea by 0.1 mm to 2 mm, preferably by 0.2 to 1.5 mm, particularly preferably by 0.5 to 1 mm. However, for certain uses of the lens according to the invention, it may be sufficient for only the radius of curvature Rcci of an inner area of the rear concave surface to meet this requirement, while the radius of curvature Rcco chosen for outer areas (lying at the lens edge) of the rear concave surface can be greater. According to the invention, the radius of curvature Rcco of the concave rear surface of the lens according to the invention lies in a range of 8.0 mm to 11.5 mm, preferably of 8.0 mm to 10 mm, particularly preferably of 8.0 to 9 mm.

According to the invention, it is preferable that the change in the radius of curvature from one zone to the next zone does not take place abruptly, but instead across an area of defined size. According to the invention, the transition from one radius of curvature to the next radius of curvature preferably takes place within a portion of the concave rear surface of the lens, which portion represents a ball segment of 0.1 mm to 0.5 mm, preferably of 0.2 to 0.3 mm.

According to the invention, the convex front surface of the lens and the concave rear surface of the lens are preferably connected to each other via an intermediate portion, which extends in a circle about the outer edge of the lens. With the aid of this intermediate portion, it is possible to maintain optimally the positioning of the lens inside the cornea and to minimize or avoid any secondary optical effects at the edge of the lens.

The intermediate portion according to the invention is characterized in that the radius of curvature of the front convex surface merges abruptly into a step at a distance of 0.005 mm to 0.01 mm, preferably of 0.6 mm to 0.008 mm from the outer edge of the lens, which step is inclined with respect to the optical axis of the lens by an angle of 15° to 45°, preferably of 20° to 40°, particularly preferably of 30°. The step has an edge length of preferably 0.01 mm to 0.015 mm, particularly preferably 0.01 mm to 0.013 mm.

Preferably, there is no intermediate portion provided on the rear surface of the lens. The radius of curvature of the outer zone of the rear surface is preferably maintained as far as the lens edge.

The intracorneal lens according to the invention has a dome shape on account of the different radii of curvature of the front convex surface and of the rear concave surface. The shape of the lens according to the invention is preferably such that the center point of the convex front surface of the lens is at a distance of 0.1 to 0.2 mm, preferably of 0.13 to 0.17 mm, from an imaginary straight line connecting the lens edges.

According to a preferred embodiment of the present invention, the intracorneal lens has a central opening, as is described in WO 2009/075685. Reference is herewith expressly made to the relevant content of WO 2009/075685.

The central opening serves for optimal positioning of the lens according to the invention in the corneal pocket and at the same time facilitates the passage of nutrient liquids and gases, for example oxygen, through the lens. The central opening is concentric to the optical axis of the lens and extends right through the lens (i.e. it is a hole and not just a depression). The size of the central opening is chosen such that the opening is still visible to the surgeon when placing the lens in the corneal pocket. At the same time, however, the opening should not be so large as to be noticeable to the person treated. In other words, the central opening should not cause optical effects of any kind. For this reason, in the case of a lens with a diameter of 3.0 mm, the central opening according to the invention preferably has a diameter of 0.12 mm to 0.2 mm, preferably of 0.13 mm to 0.17 mm, and particularly preferably of 0.15 mm. Smaller openings are unable to meet the demands described above, while larger openings lead to optical effects that are noticed by the person treated, which is undesirable according to the invention. Generally speaking, the central opening of the lens according to the invention should only occupy a proportion of the area of the front surface of less than 1%, preferably of less than 0.5%.

According to the present invention, the central opening typically has a cylindrical shape. As a result of the lens thickness at the position of the central opening, the opening has a length through the lens of 0.01 to 0.1 mm, preferably of 0.015 mm to 0.05 mm, and particularly preferably of 0.02 to 0.03 mm. However, other shapes of hole can also be chosen, of the kind described in WO 2009/075685 and incorporated herewith by reference. Conical openings may be mentioned by way of example, or openings that have sections of different diameter.

At the center of the lens (i.e. at its optical axis), the lens according to the invention preferably has a thickness of 0.01 to 0.1 mm, preferably of 0.015 mm to 0.05 mm, and particularly preferably of 0.02 to 0.03 mm.

As has been described above, the lens according to the invention can have different zones with different optical power. The number of different optical zones is dependent here on the desired corrective effect that is intended to be achieved using the lens according to the invention.

In a preferred embodiment according to the invention, the intracorneal lens has two optical zones. A first inner area extends in a circle around the center of the lens and has no optical power (non-optical area). For some uses, however, it may be entirely desirable that the inner area has a slight optical power, for example of less than 1 diopter, preferably 0.1 to 0.8 diopter, particularly preferably 0.1 to 0.6 diopter. For other uses, an optical power of well over 1 diopter may even be chosen. According to the invention, the inner area preferably has a diameter of 1.4 mm to 2.4 mm (depending on the diameter of the lens). With a lens diameter of 3 mm, the inner area should preferably have a diameter of 1.5 to 2.0 mm, particularly preferably of 1.8 mm.

A circular second optical area is arranged around the inner optical area. The second, outer area has an optical power which is dependent on the desired sight correction that is intended to be achieved using the lens according to the invention. Generally speaking, the optical power of the second, outer area is greater than 1 diopter.

The diopter values indicated above relate to the optical power that is made available by the lens in the implanted state, i.e. in the hydrated state, in the cornea.

According to a further embodiment of the present invention, the intracorneal lens can also be configured as a diffractive lens. Diffractive lenses are known from the prior art. Reference is made by way of example to WO 2009/075685 or to EP 1 001 720 B1. A diffractive lens is preferably configured in such a way that it has several circular optical zones that merge into each other via steps. This is shown, for example, in FIGS. 12 and 13 of WO 2009/075685. Reference is made expressly to the relevant content of WO 2009/075685.

According to a further embodiment of the present invention, the intracorneal lens can also be configured in such a way that, in terms of its optical power, it has a gradient. This can be achieved, for example, by the lens being made from different materials with different refractive indices gradually merging into one another. Alternatively, the refractive index of a material can also be gradually changed by suitable measures such as irradiation with high-energy electromagnetic radiation.

In light of the different configuration of the front surface and of the rear surface of the intracorneal lens according to the invention, it is extremely important that the intracorneal lens according to the invention is inserted correctly into the pocket provided for it in the cornea, i.e. with the front surface of the lens toward the outside of the eye and with the rear surface of the lens toward the interior of the eye.

Correct insertion of the lens according to the invention into a pocket provided for it in the cornea can particularly preferably be achieved, according to the invention, using an applicator of the kind described in WO 2011/069907 A1. Reference is herewith expressly made to the relevant content of WO 2011/069907 A1.

WO 2011/069907 A1 describes an applicator comprising a grip piece and a pre-load unit. Grip piece and pre-load unit can be connected to each other, preferably with the aid of a bayonet connection secure against rotation. The pre-load unit can first be equipped with a lens, such as the lens according to the invention, and stored in a sterile manner in a storage unit. To insert the lens, the physician removes the pre-load unit from the storage unit and connects the pre-load unit to the grip piece. The lens can then be inserted into the corneal pocket in the manner described in WO 2011/069907 A1.

The present invention thus also relates to a kit comprising a storage unit and a pre-load unit in the interior of the storage unit, wherein the storage unit is made of a watertight material and can be closed in a watertight manner with a stopper, and the pre-load unit is fitted with an intracorneal lens according to the invention.

The pre-load unit is preferably designed for one-off use. The pre-load unit is equipped with the intracorneal lens according to the invention and is stored in a sterile package, from which it is only removed, and connected to the grip piece, directly before the insertion of the lens into the eye.

To be able to store the pre-load unit in a sterile state over a long period of time, it is packaged in a storage unit that protects the pre-load unit from environmental influences. For this purpose, the interior of the storage unit is filled with a storage liquid, which constantly covers at least the lens located in the chamber of the pre-load unit. This storage liquid can be water. However, the storage liquid is preferably physiological saline (NaCl).

The storage unit is made from a material that is watertight and therefore also allows only very little water vapor, if any, to pass through. This is important in order to ensure a sufficient level of storage liquid within the storage unit during the entire storage period. If the material were not watertight, the storage liquid would evaporate over a certain time, and the lens in the chamber of the pre-load unit would no longer be stored in a sterile state. Watertight materials are known to a person skilled in the art. Examples of such a material are glass or a watertight plastic. After introduction of the pre-load unit, the storage unit is closed in a watertight manner by means of a suitable stopper. This stopper is preferably made from a watertight plastic.

The top face of the pre-load unit is clearly identified, for example with a suitable inscription such as "TOP". Since the pre-load unit is equipped with the lens according to the invention in such a way that the convex front surface of the lens points in the direction of the identified top face of the pre-load unit, the surgeon has no problem in correctly inserting the lens into the pocket in the cornea. He simply has to fit the pre-load unit onto the grip piece, i.e. with the identified top face of the pre-load unit facing upward.

The pre-load unit is described in detail in WO 2011/069907 A1. Reference is herewith expressly made to the relevant content of WO 2011/069907 A1. The pre-load unit for inserting lenses into the eye of a human or animal comprises i) a housing with means for fastening the unit to a grip piece, preferably in a manner secure against rotation, ii) a lens-receiving part arranged on or in the housing and comprising a section that protrudes from the housing and that has preferably exactly two separate leaf-like units which, at least at their ends directed away from the housing, are in releasable contact with each other and there form a chamber for storing an optical lens, iii) a slide, which is arranged movably in the interior of the housing and can be moved between the leaf-like units of the lens-receiving unit.

According to the present invention, a leaf-like unit is to be understood as a structural part which is very thin, similarly to a leaf, and thus has corresponding flexibility. According to the present invention, the leaf-like units typically have a thickness of between 0.1 and 0.3 mm and typically have a length of 20-40 mm, preferably 20 to 30 mm. The material used for the leaf-like units is a physiologically compatible plastic or a physiologically compatible metal.

The two leaf-like units preferably each have exactly one hole, and the holes are arranged such that they lie directly over each other and form an opening through the center of the chamber for storing an optical lens. In this way, a lens located in the chamber can be positioned particularly easily on the optic axis of the eye. The person inserting the lens sees the lens through the opening and can align it exactly. These holes can typically have a diameter of 0.3 to 0.6 mm.

This embodiment is particularly advantageous for intracorneal lenses with a central hole, as have been described above.

The leaf-like units of the lens-receiving part, at their ends directed away from the housing, form a chamber for storing the lens according to the invention. The leaf-like units are in loose contact with each other in the area of the chamber, i.e. they can be moved apart from each other by application of force, in order to open the chamber for the purpose of inserting or removing the lens according to the invention. The leaf-like units are spread apart from each other by means of a slide. The chamber is at least partially bounded by wave-shaped sections, which are present on both leaf-like units and are arranged such that the sections of one leaf-like unit mesh with the corresponding sections of the other leaf-like unit. In the state of contact between the two leaf-like units, the lens cannot slip out of the chamber.

With the applicator described in WO 2011/069907 A1, the lens is not ejected into a corneal pocket, and instead the applicator is positioned exactly in the corneal pocket and then, with the lens maintained in position, the leaf-like parts are drawn back by an exactly defined distance. For this purpose, the section of the pre-load unit of the applicator in which the chamber for storing the lens according to the invention is formed must be configured in such a way that it can be inserted into a corresponding corneal pocket. The shape of the area of the applicator forming this chamber preferably corresponds substantially to the shape of the lens to be inserted, or it is even slightly smaller in width than the corresponding lens. This is possible, for example, by the chamber not having a round shape and not having the above-described boundaries all around, i.e. the chamber is laterally open between the boundaries. The lens located in the chamber can then protrude from the chamber at some points.

In order to fit the pre-load unit with the lens according to the invention, the leaf-like units are spread apart from each other in order to permit access to the above-described chamber. According to one embodiment of the present invention, this can be done by inserting a suitable tool, for example a knife, into a lateral gap between the leaf-like units. The lens is then placed in the accessible chamber, preferably under a microscope. The tool is then removed from the lateral gap between the leaf-like units, as a result of which the leaf-like units again come into contact with each other at their ends and the chamber is closed. For the loading procedure, it is possible, for example, to provide a loading station in which the pre-load unit can be fixed. The loading station has a rotatable tool (e.g. a knife), which can be rotated into the lateral gap between the leaf-like units and rotated back out of said gap.

After it has been removed from the storage unit, the pre-load unit is fitted onto the grip piece, which is likewise described in detail in WO 2011/069907 A1. Reference is herewith expressly made to the relevant content of WO 2011/069907. The applicator is typically an elongate tube with a shape that ensures the grip piece can be easily held in the hand. The grip piece is designed at one end in such a way that the pre-load unit and the grip piece can be connected to each other such that the pre-load unit can be moved inside the grip piece. For this purpose, the grip piece has a diameter exceeding the diameter of the part of the pre-load unit that is to be inserted into the grip piece. The grip piece is hollow on the inside, at least at the end to be connected to the pre-load unit. However, it is preferably a completely hollow tube.

A slide is arranged movably inside the pre-load unit and the grip piece. This slide must be able to be moved forward between the leaf-like units to such an extent that it comes into contact with the lens located in the chamber and can fix this lens. The slide preferably tapers toward the end that is to move between the leaf-like units. To better fix the lens, the front end of the slide is correspondingly designed to complement the lens shape.

The slide and the pre-load unit are moved with the aid of control elements, which are arranged on the grip piece. This is described in detail in WO 2011/069907 A1. Reference is herewith expressly made to the relevant content of WO 2011/069907.

The grip piece of the applicator according to the invention is preferably intended to be used more than once. For this purpose, according to a preferred embodiment of the present invention, the grip piece can be completely dismantled, such that all the structural parts can be completely cleaned and sterilized. However, according to an alternative embodiment of the present invention, the grip piece can likewise be provided for one-off use. According to this embodiment, the grip piece is preferably stored separately until use, likewise in a storage unit analogous to the above-described unit. However, according to this embodiment, it is also conceivable that the pre-load unit and the grip piece are already stored as a unit until use (either separately, as described above, or also fixedly connected to each other), in a storage unit analogous to the above-described unit. According to this alternative embodiment, the applicator can therefore be constructed differently in that the parts for connecting grip piece and pre-load unit can be replaced by a fixed connection of these structural parts.

With the aid of the above-described applicator from WO 2011/069907 A1, the lens according to the invention can be easily inserted into a pocket in the cornea. The insertion method comprises the steps of:

a) positioning the above-described applicator in the correct orientation at the desired location of the eye, preferably in a pocket in the human cornea, such that the center of the optical lens contained in the applicator lies on the optic axis of the eye;

b) pushing the slide forward by means of a first control element on the grip piece, until the slide comes into contact with the lens without moving the latter, wherein at the same time the leaf-like units of the lens-receiving part are spread apart from each other;

c) withdrawing the rest of the pre-load unit by a defined distance by means of a second control element on the grip piece, with simultaneous fixing of the slide, as a result of which the lens is released from the applicator.

The pre-load unit, preferably stored in a sterile state, is removed from the storage container and connected to the grip piece, preferably in a manner secure against rotation. The applicator thus obtained, fitted with the lens according to the invention, is then positioned at the desired location of the eye. For this purpose, the ends of the leaf-like units of the pre-load unit which form the chamber, with the lens according to the invention located therein, are inserted into a pocket that has been created beforehand in the cornea of an eye. According to a particularly preferred embodiment of the present invention, the pre-load unit has an opening extending through the chamber with the lens. This allows the person performing the procedure to align the lens exactly on the optic axis of the eye while the lens is still located in the chamber of the applicator. As has been explained above, it is extremely important that the applicator, and therefore the lens located in the applicator, is inserted correctly into the corneal pocket. This is achieved by clear identification of the top face of the pre-load unit with the lens placed correctly therein. The surgeon has to ensure that the applicator correctly equipped with the lens (i.e. with the front surface of the lens pointing toward the clearly identified top face of the pre-load unit) is inserted correctly into the corneal pocket, i.e. with the identified top face of the pre-load unit pointing upward (away from the interior of the eye).

The lens is then fixed inside the applicator by means of the first control element on the grip piece being pushed fully forward, as a result of which the slide of the pre-load unit is moved forward to the maximum extent, such that it comes into contact with the lens located in the chamber. This is made possible by the fact that, as a result of the forward movement of the slide, the leaf-like units are spread apart from each other and the interior of the chamber thus becomes accessible. In the next step, the rest of the pre-load unit, except for the slide, is drawn back from the eye by a defined distance with the aid of the second control element, with the rest of the pre-load unit being drawn into the grip piece. During this step, the slide remains fixed and thus holds the lens exactly at the previously aligned position.

By means of the rest of the pre-load unit being drawn back, the lens is released from the applicator exactly in the previously aligned position. The lens is thus already placed in the eye as desired. A further aligning step is no longer required. The applicator is then removed from the eye and dismantled into its individual parts. The pre-load unit intended for one-off use is now preferably disposed of, while the grip piece is dismantled and cleaned, such that it is available for the next use with a new pre-load unit.

Methods for generating pockets in the cornea for implantation of intracorneal lenses are known. For example, reference is made to specific cutting instruments (microkeratomes), as are described in EP 1 778 141 A1, and to laser techniques. The creation of pockets in the cornea with the aid of lasers (such as pulsed lasers) is described, for example, in US 2003/0014042 or in WO2008/072092 A1. Particularly with the aid of lasers, corneal pockets can be created with a very precise cutting depth, as a result of which it is possible to achieve a very exact positioning of the lenses according to the invention and, by association, a very precise correction of the corresponding sight defect.

Figure 2:
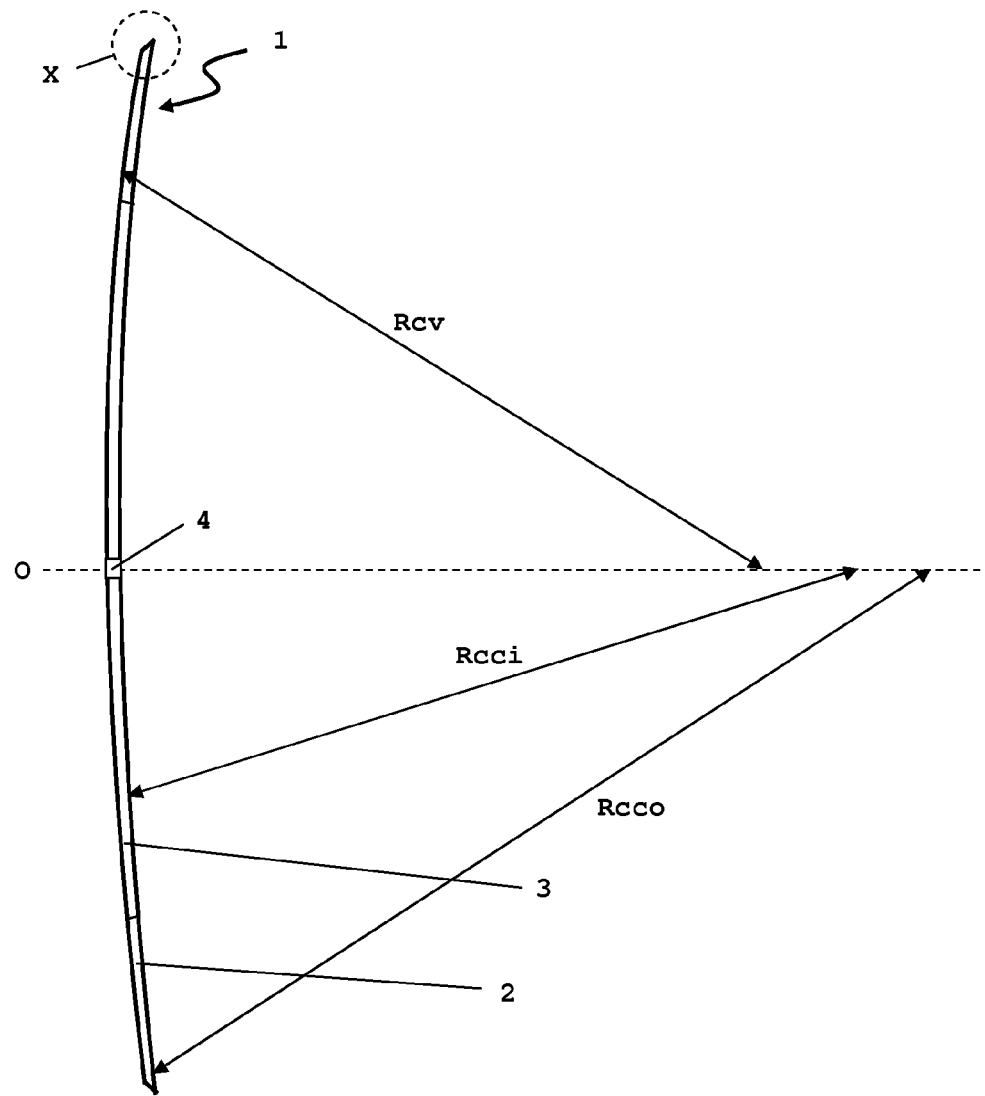
Figure 3:
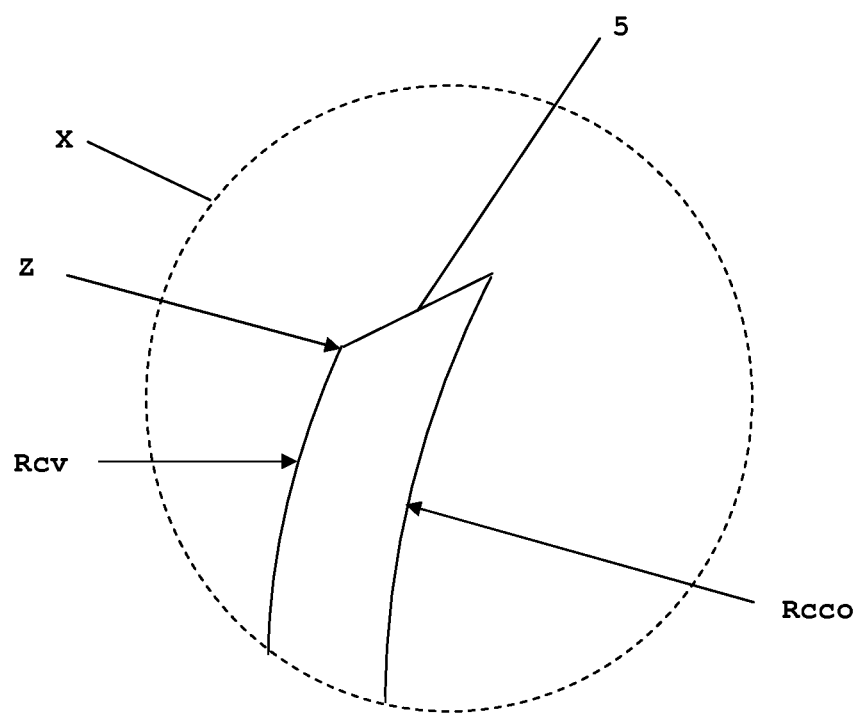
Figure 4:
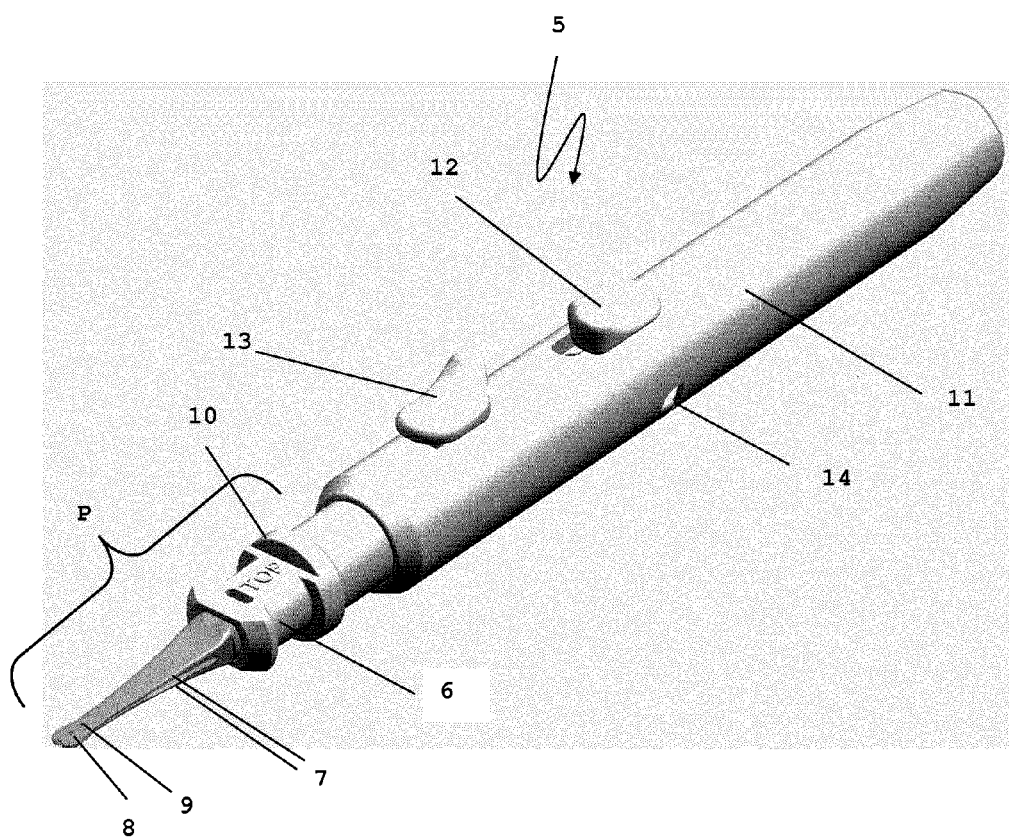
Figure 5:
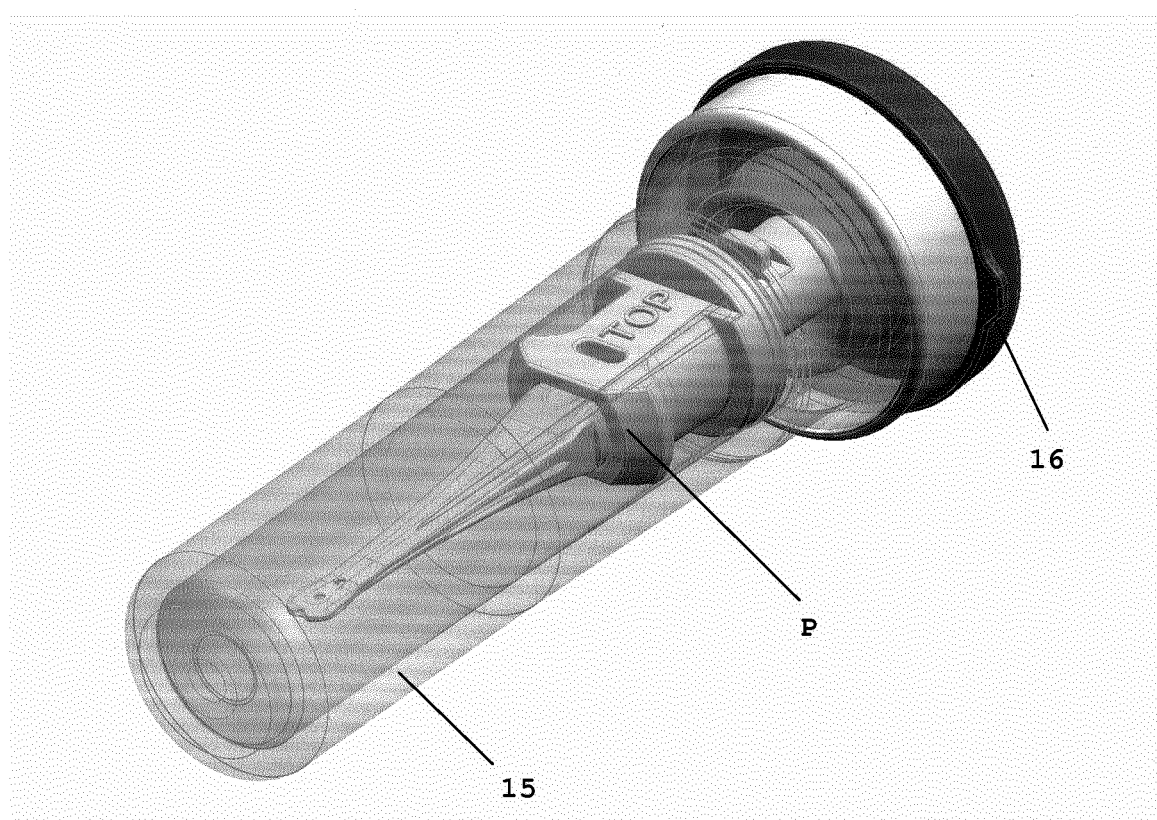
Figure 6:
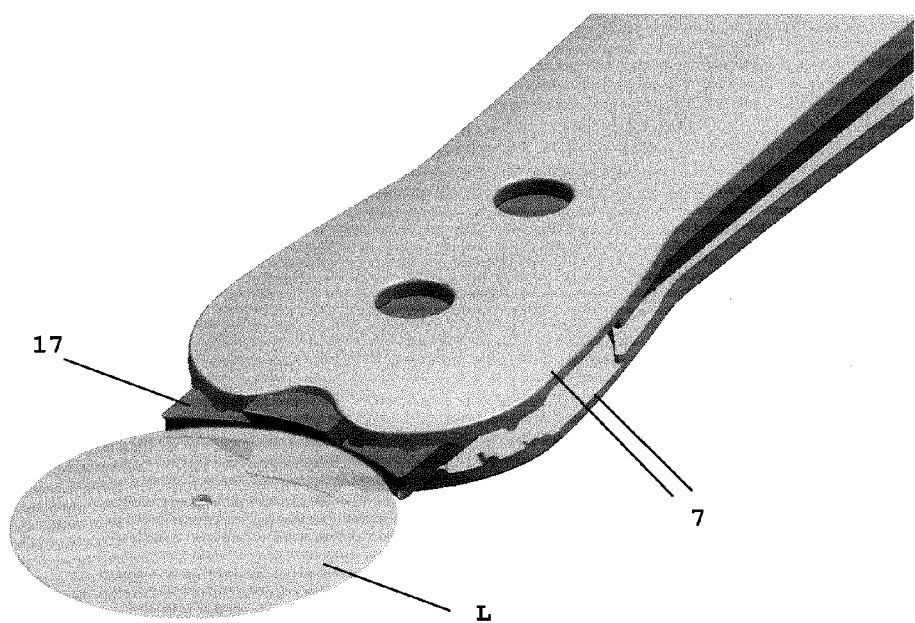

The present invention is explained in more detail below with reference to non-limiting drawings and examples. In the drawings:

FIG. 1 shows a front view of an embodiment of an intracorneal lens according to the invention, FIG. 2 shows a side view (not true to scale) of the intracorneal lens according to the invention from FIG. 1, FIG. 3 shows an enlarged view of the detail X of the intracorneal lens according to the invention from FIG. 2, FIG. 4 shows an embodiment of the applicator according to WO 2011/069907 A1 for inserting the lens according to the invention into a corneal pocket, FIG. 5 shows an embodiment of the kit according to WO 2011/069907 A1 for storing the pre-load unit equipped with the lens according to the invention, FIG. 6 shows a detail view of the function of the applicator according to WO 2011/069907 A1.

A front view of an embodiment of an intracorneal lens 1 according to the invention is shown in FIG. 1. In this embodiment, the lens 1 has a diameter of 3.0 mm. The lens has an outer optical area 2 which, in this embodiment, has an optical power of 1.25 diopters (in the cornea). Moreover, the lens 1 has an inner area 3 which, in this embodiment, has a diameter of 1.8 mm and no optical power or, in other uses, an optical power of at most 0.5 diopter. The lens 1 additionally has a central opening 4. The latter is concentric to the optical axis of the lens 1 and, in this embodiment, has a diameter of 0.15 mm.

A side view of an embodiment of an intracorneal lens 1 according to the invention is shown in FIG. 2. The radii of curvature are not shown true to scale in FIG. 2. The lens 1 has a convex front surface with a single uniform radius of curvature Rcv. The different zones 2 and 3 are identified by different radii of curvature Rcco and Rcci on the concave rear surface of the lens 1. In the embodiment according to FIG. 2, the radii of curvature have the following values: Rcv: 7.8 mm; Rcco: 8.858 mm; Rcci: 8.192 mm. The radius of curvature Rcco merges into the radius of curvature Rcci within a circle segment of 0.027 mm on the rear surface of the lens 1. Concentrically with respect to the optical axis O, a central opening 4 is formed in the lens 1 and has a depth of 0.0259 mm. The convex front surface of the lens 1 is connected to the concave rear surface of the lens 1 via an intermediate portion which is located in the area at the lens edge identified by the circle X in broken lines.

FIG. 3 shows an enlarged view of the intermediate portion of the lens 1 according to the invention shown by the circle X in broken lines in FIG. 2. The front convex surface of the lens 1 has the radius of curvature Rcv as far as a point Z on the front surface of the lens 1. In the embodiment according to FIG. 3, this point Z is located 0.0078 mm below the edge of the lens 1. Starting from the point Z, the front surface of the lens 1 has a straight shape. This straight portion connects the point Z on the front surface of the lens 1 to the lens edge where the rear surface of the lens 1 with the radius of curvature Rcco has its origin. In the embodiment according to FIG. 3, the straight portion between the point Z and the lens edge is inclined by 30° in relation to the optical axis O of the lens. In the embodiment according to FIG. 3, the straight portion has a length of 0.012 mm.

FIG. 4 shows an embodiment of the applicator 5 from WO 2011/069907 A1. A pre-load unit P is mounted movably in the grip piece 11. The pre-load unit P comprises a housing 6, two leaf-like units 7 and a stop 10, which limits the movement of the pre-load unit P into the grip piece 11. In the leaf-like units 7, a continuous opening 8 is present through the center of the chamber (not shown here) for receiving a lens. A further hole 9, which makes it easier to equip the applicator 7 with the lens according to the invention, is additionally provided. Two control elements 12 and 13 are mounted on the grip piece 11, by means of which control elements 12 and 13 the pre-load unit P and a slide (not shown in FIG. 4) in the interior of the pre-load unit P and of the grip piece 11 can be moved. A pin, protruding from the lateral opening 14, is fastened to insert parts present in the grip piece and fixes these parts in the grip piece 11. The top face of the pre-load unit P is clearly marked with the word "TOP".

FIG. 5 shows an embodiment of the kit according to WO 2011/069907 A1, which comprises a storage unit 15. In the interior of the storage unit 15, the pre-load unit P is stored in physiological saline. The storage unit 15 is made of glass. It is closed in a watertight manner with a stopper 16.

FIG. 6 shows how a lens L is released from the pre-load unit according to WO 2011/069907 A1. The slide 17 is pushed forward until it is in contact with the lens L. The leaf-like units 7 are thereby spread apart from each other. The leaf-like units 7 can now be drawn back by a defined distance, while the slide 17 holds the lens L at the previously oriented site. The lens L is then released, and the applicator according to the invention can be removed.

An intracorneal lens according to the invention, of the kind described in FIGS. 1 to 3, was implanted in a group of 28 test subjects. Thereafter, in a standard sight test, the subjects were able to detect a resolution of approximately 4 line pairs per mm from a distance of 25 cm. For comparison purposes using an intracorneal lens according to WO 2009/075685, it is known that, with a conventional lens of this kind, it is possible to achieve only a resolution of approximately 2 line pairs per mm in the same test.

The invention claimed is:

1. An intracorneal lens for a cornea, said cornea having an average radius which lies within a range of 7.4 mm to 8.1 mm, the intracorneal lens comprising
  a circular main body with a convex front surface and a concave rear surface;
  said convex front surface having a single uniform radius of curvature (Rcv);
  said concave rear surface having at least first and second zones, wherein the first zone has a radius of curvature (Rcci) furnishing an optical power in the first zone ranging from 0 to 0.5 diopters and the second zone has a radius of curvature (Rcco) furnishing an optical power in the second zone of 1.25 diopters; and
  said radius of curvature (Rcci) of said concave rear surface is greater than the average radius of the cornea by 0.1 mm to 2 mm.

2. The intracorneal lens of claim 1, wherein said lens has a central opening which is concentric to an optical axis and which occupies a proportion of the area of the front surface of less than 1%.

3. The intracorneal lens of claim 1, wherein said circular main body has a diameter in the range of 2.4 to 4 mm.

4. The intracorneal lens of claim 1, wherein said lens has, in the area of its optical axis, a thickness in the range of 0.01 to 0.1 mm.

5. The intracorneal lens of claim 1, wherein said convex front surface and said concave rear surface are connected to each other via an intermediate portion at an outer edge of the circular main body.

6. The intracorneal lens of claim 1, wherein said lens is a diffractive lens.

7. The intracorneal lens of claim 1, wherein said has a power gradient lens.

8. The intracorneal lens of claim 1, wherein said radius of curvature (Rcci) is smaller than said radius of curvature (Rcco).

* * * * *